(12) United States Patent
Navarro-Paredes et al.

(10) Patent No.: US 8,909,336 B2
(45) Date of Patent: Dec. 9, 2014

(54) EXTERNAL DEFIBRILLATOR

(75) Inventors: Cesar Oswaldo Navarro-Paredes, Newtownabbey (GB); John McCune Anderson, Hollywood Down (GB); Janice Anderson, legal representative, Hollywood Down (GB)

(73) Assignee: Heartsine Technologies Limited, Belfast (GB)

( * ) Notice: Subject to any disclaimer, the term of this patent is extended or adjusted under 35 U.S.C. 154(b) by 0 days.

(21) Appl. No.: 13/990,059

(22) PCT Filed: Nov. 25, 2011

(86) PCT No.: PCT/EP2011/071069
§ 371 (c)(1),
(2), (4) Date: May 29, 2013

(87) PCT Pub. No.: WO2012/072518
PCT Pub. Date: Jun. 7, 2012

(65) Prior Publication Data
US 2013/0245708 A1    Sep. 19, 2013

(30) Foreign Application Priority Data

Nov. 29, 2010 (IE) .................................. S2010/0746

(51) Int. Cl.
| | |
|---|---|
| *A61N 1/00* | (2006.01) |
| *A61B 5/00* | (2006.01) |
| *A61B 5/0452* | (2006.01) |
| *A61N 1/39* | (2006.01) |
| *A61B 5/053* | (2006.01) |

(52) U.S. Cl.
CPC ............ *A61N 1/3925* (2013.01); *A61B 5/7239* (2013.01); *A61B 5/0452* (2013.01); *A61B 5/721* (2013.01); *A61B 5/7207* (2013.01); *A61N 1/3931* (2013.01); *A61B 5/0535* (2013.01)
USPC ............................................................ 607/7

(58) Field of Classification Search
CPC .................................................... A61N 1/3925
USPC ............................................................ 607/7
See application file for complete search history.

(56) References Cited

U.S. PATENT DOCUMENTS

| | | |
|---|---|---|
| 4,619,265 A | 10/1986 | Morgan et al. |
| 5,247,939 A | 9/1993 | Sjoquist et al. |

(Continued)

FOREIGN PATENT DOCUMENTS

| | | |
|---|---|---|
| EP | 2 171 245 A1 | 4/2010 |
| WO | WO 2009/109595 A1 | 9/2009 |

*Primary Examiner* — Robert N Wieland
(74) *Attorney, Agent, or Firm* — Novak Druce Connolly Bove + Quigg LLP

(57) ABSTRACT

An external defibrillator includes patient electrodes (20) for obtaining the patient's electrocardiogram (ECG) and for applying a shock to the patient. A microprocessor (24) analyses the patient's ECG using a diagnostic algorithm to detect if the patient's heart is in a shockable rhythm, and shock delivery circuitry (10) is enabled when a shockable rhythm is detected by the diagnostic algorithm. The patient electrodes also allow obtaining a signal (Z) which is a measure of the patient's transthoracic impedance and the microprocessor is responsive to Z to detect conditions likely to cause the diagnostic algorithm to generate a false detection of a shockable rhythm. If such detection is made, the microprocessor prevents detection of a shockable rhythm by the diagnostic algorithm, at least for a period of time.

20 Claims, 3 Drawing Sheets

(56) References Cited

U.S. PATENT DOCUMENTS

| | | |
|---|---|---|
| 6,287,328 B1 | 9/2001 | Snyder et al. |
| 2006/0025825 A1 | 2/2006 | Bowers |
| 2011/0224746 A1 | 9/2011 | Didon |
| 2012/0302896 A1 * | 11/2012 | Joo et al. .................... 600/479 |

* cited by examiner

US 8,909,336 B2

EXTERNAL DEFIBRILLATOR

This invention relates to an external defibrillator.

External automated defibrillators are normally connected to a patient via two electrodes. An electrocardiogram (ECG) and the patient's transthoracic impedance (ICG) are continuously recorded by the defibrillator and analysed using a diagnostic algorithm in order to detect a shockable rhythm, e.g. ventricular fibrillation (VF). If such a rhythm is found, the defibrillator prompts an audible/visible message to the operator (rescuer) to activate the defibrillator to deliver a therapeutic shock which may allow the patient to regain a perfused rhythm.

The use of a defibrillator involves a stressful time for the operator where the patient requires a fast and adequate treatment. The patient could be moved during preparation for CPR or checking for vital signs, etc., or the electrodes could be inadvertently touched after their application to the patient and while the ECG is being analysed. Any of these actions can introduce noise into the ECG and ICG signals being acquired by the defibrillator through the attached electrodes. This signal noise can mislead the diagnostic algorithm and cause it to generate a false determination of a shockable rhythm. This represents a risk to the patient when a non-shockable rhythm is wrongly classified as a shockable one and a risk to the operator when a shock is delivered while manipulating the patient.

It is therefore desirable that lay responders using public access defibrillators are provided with more reliable and safer devices.

According to an aspect of the present invention, there is provided an external defibrillator as specified in Claim 1.

According to the invention there is provided an external defibrillator including patient electrodes for obtaining the patient's electrocardiogram (ECG) and for applying a shock to a patient, circuit means for analysing the patient's ECG using a diagnostic algorithm to detect if the patient's heart is in a shockable rhythm, and shock delivery circuitry which is enabled when a shockable rhythm is detected by the diagnostic algorithm, wherein the patient electrodes also allow obtaining a signal (Z) which is a measure of the patient's transthoracic impedance and the circuit means is responsive to Z to detect interference conditions likely to cause the diagnostic algorithm to generate a false detection of a shockable rhythm and, if such detection is made, to prevent detection of a shockable rhythm by the diagnostic algorithm, at least for a period of time.

In a preferred embodiment the circuit means detects said conditions by forming the first derivative dZ/dt of Z, deriving a quantity related to the energy of dZ/dt in a moving time window, and determining if said energy-related quantity exceeds a certain threshold level.

The present invention uses the patient's transthoracic impedance to detect when a faulty classification is likely to occur, since the impedance signal is more sensitive to interferences such as movement of the patient and touching electrodes by the operator than the ECG. Dramatic changes observed in the patient's impedance are strong indicators of interferences such as those mentioned above taking place.

An embodiment of the invention will now be described, by way of example, with reference to the accompanying drawings, in which.

Figure 1:
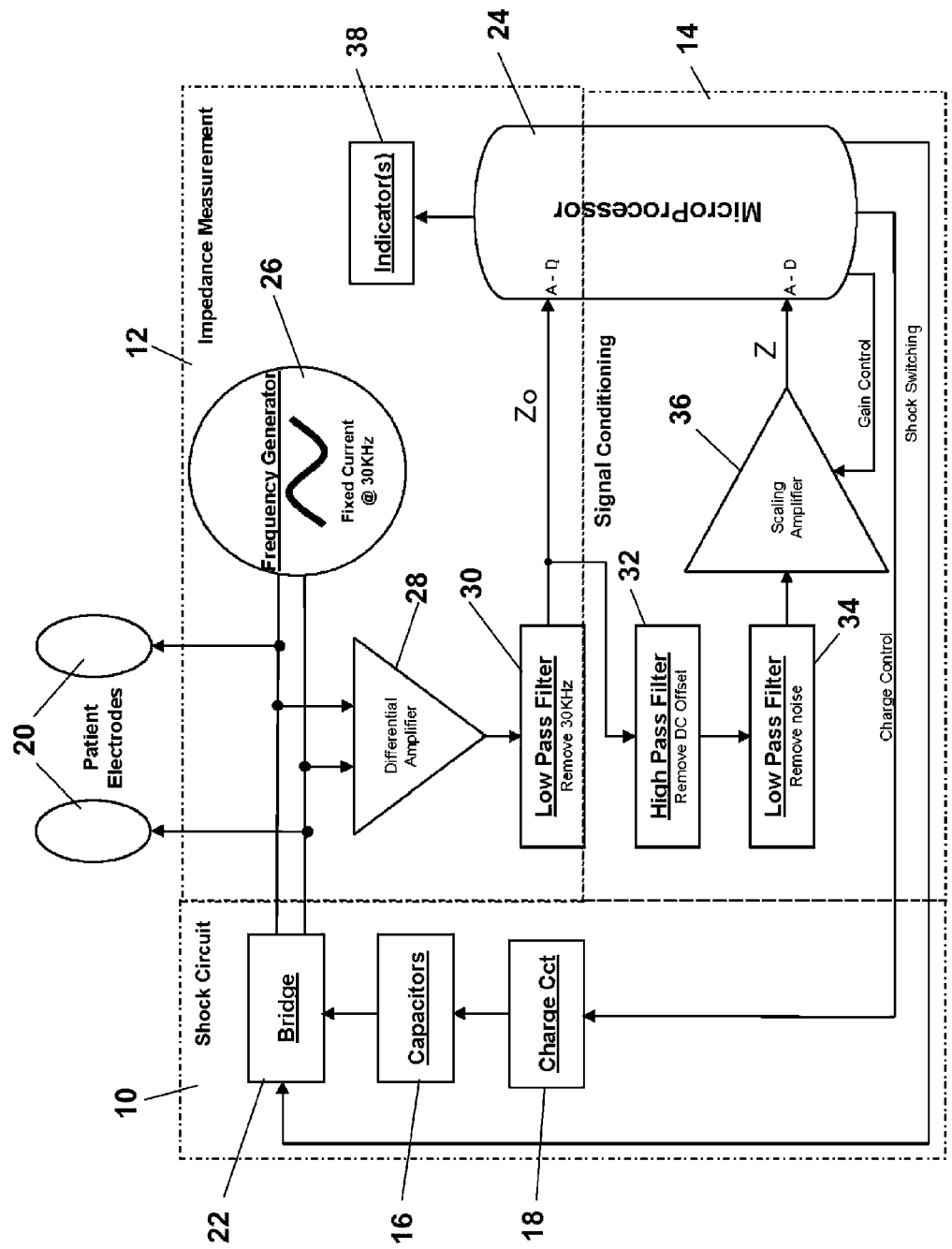
FIG. 1 is a block diagram of an automated external defibrillator embodying the invention.

Referring to FIG. 1, an automated external defibrillator comprises three main sections: 10, 12 and 14.

Section 10 is the main high voltage shock circuitry and comprises a bank of capacitors 16 which are charged up to a high voltage by a charging circuit 18, the charge being released as a bi-phasic high voltage shock through a pair of patient electrodes 20 by a bridge circuit 22. The charging of the capacitors 16 and the shape and duration of the bi-phasic shock waveform is controlled by a microprocessor 24, the actual shock being given by the user pressing a button (not shown) if the patient's condition is deemed "shockable" as determined by a diagnostic algorithm having the patient's ECG as input. The ECG is derived from the patient electrodes 20 in known manner, not shown. The process is prompted by voice messages and/or visual prompts output on visual/audio indicators 38 (the indicators are shown in section 12 for diagrammatic simplicity). The audio/visual output indicators 38 may comprise a loudspeaker and/or LED(s).

Section 12 measures the patient's transthoracic impedance using the same electrodes 20 as are used for applying the shock. A generator 26 produces a 30 kilohertz sinusoidal waveform at a constant current of 100 microamperes. This signal is applied across the electrodes 20. When the electrodes are attached to a patient, a voltage across the electrodes is generated which is superimposed on the 30 kHz sinusoid. This voltage is a direct measurement of the transthoracic impedance of the patient. The voltage generated in response to the sinusoid is applied to a differential amplifier 28 which converts it from a differential signal to a single signal referenced to ground potential. The resultant waveform is passed through a low pass filter 30 which removes the original 30 kHz signal leaving a signal Zo (static impedance) which is directly proportional to the patient impedance. The impedance signal Zo is used by the microprocessor 24 to set the bi-phasic pulse amplitude and width to ensure that the correct total energy (typically 150 Joules) is delivered to the patient.

The construction and operation of sections 10 and 12 of the AED are well-known, and it is not thought that further detail is necessary.

The purpose of section 14 is to provide further conditioning of the impedance signal Zo as input to an algorithm to detect circumstances likely to cause the main diagnostic algorithm to generate a false detection of a shockable rhythm. Section 14 is additional to the existing circuitry for the derivation of patient impedance in section 12.

In section 14 of the defibrillator the impedance signal Zo which is output from the low pass filter 30 is passed through a high pass filter 32 which removes the dc offset before removing higher frequency noise in the low pass filter 34. Finally the signal is scaled in an amplifier 36 incorporating digital gain control to a level appropriate for analogue-to-digital conversion by the microprocessor 24. The resultant filtered and amplified signal Z is digitally converted. In this embodiment the analog to digital sample rate is 170.66 samples per second. However, this is not a limitation for the detection of interference since adjustments in thresholds are possible to adapt to a different sample rate. The impedance signal Z is differentiated and the result dZ/dt is used in an algorithm, FIG. 3, to detect interference conditions likely to cause the diagnostic algorithm to cause it to generate a false detection of a shockable rhythm.

Figure 2:
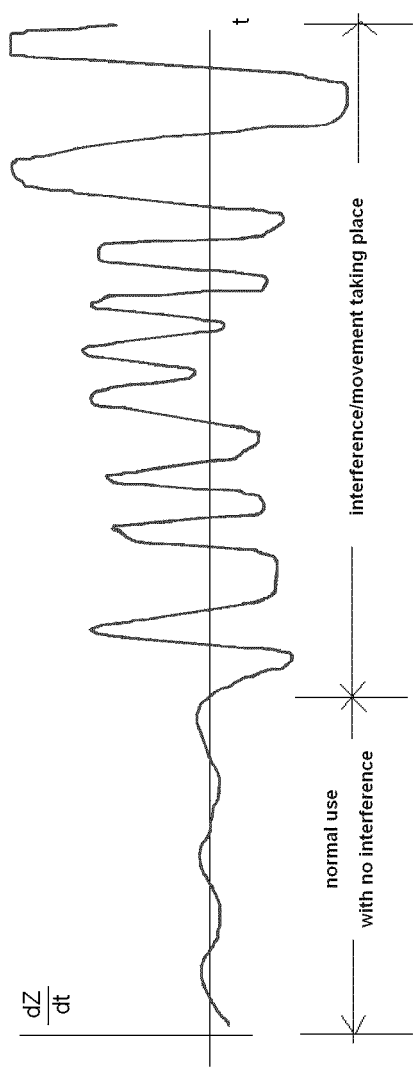
FIG. 2 is an impedance waveform illustrating the first derivative dZ/dt of the impedance signal Z during periods of no interference and interference respectively.
Figure 3:
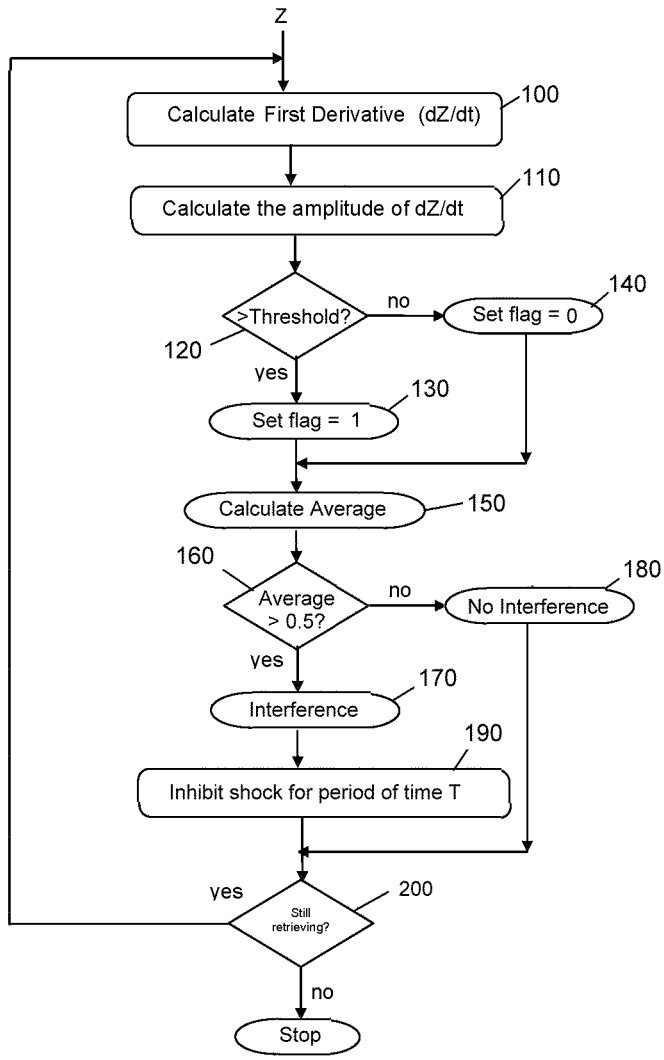
FIG. 3 is a flow diagram of an algorithm to detect conditions likely to cause the diagnostic algorithm to generate a false detection of a shockable rhythm.

First, however, reference is made to FIG. 2 which shows a typical dZ/dt waveform during periods of no interference and interference respectively. On the left the signal has a relatively low energy, corresponding to a period when the patient and the electrodes are undisturbed. On the right, however, the signal becomes relatively much more energetic, corresponding to a period when the patient and/or electrodes are disturbed sufficiently to cause, or be likely to cause, the diagnostic algorithm to generate a false detection of a shockable rhythm. The algorithm of FIG. 3 is therefore designed to detect periods when the energy of dZ/dt is above a threshold level likely to cause false detection. In particular, in the preferred embodiment, the algorithm detects disturbances likely to cause the diagnostic algorithm to generate a false detection of a shockable rhythm by forming the first derivative of Z (dZ/dt), deriving a signal related to the energy of dZ/dt in a moving time window, and determining if the energy signal exceeds a certain (empirically determined) threshold level.

Referring now to FIG. 3, in respect of successive (preferably consecutive) digital values of Z input to the microprocessor 24 from the scaling amplifier 36 the algorithm performs the following steps for each such value:

a. At step 100 the signal Z is differentiated by software in the microprocessor 24 to obtain its first derivative dZ/dt.
b. Next, step 110, the amplitude of dZ/dt is calculated.
c. Next, step 120, if the amplitude of the signal dZ/dt is greater than a certain threshold a flag is set to 1, step 130, otherwise the flag is set to 0, step 140.
d. The flag values (0 or 1) are averaged over the last 0.75 s, step 150. This is done by feeding a binary array of 128 elements (equivalent to 0.75 s using a 170.66 sample rate). The oldest value in the array is substituted by the newest one, and the elements of the binary array are summed and divided by 128.
e. If this average is greater than 0.5, step 160, which means that most of the time dZ/dt has been higher than the threshold, the algorithm flags that it has detected interference or disturbance likely to cause the diagnostic algorithm to generate a false detection of a shockable rhythm (step 170). Otherwise no interference or disturbance is detected, step 180.
f. In the case of interference being found at step 170 the diagnostic algorithm in the defibrillator is prevented from detecting a shockable rhythm for a period of, in this embodiment, 4 seconds (step 190).

The process continues (step 200) until no more Z values are input, i.e. the Z signal is no longer present.

The threshold value used in step 120 of this embodiment was obtained empirically by analysing a large volume of patient data when interferences was documented. Additionally, the threshold value depends on the A-D sample rate, the gain from the amplifier 36, the resolution of Z, the length of the moving time window, the technique used for calculating dZ/dt, etc.

It will be evident that in this embodiment the average calculated at step 150 is a measure of the energy of the dZ/dt signal over the preceding 0.75 s window. That is to say, the more often the amplitude of dZ/dt exceeds the threshold in the moving window, the greater the energy of the signal.

However, other methods of measuring the energy of the signal in a moving time window can be used in other embodiments of the invention. For example, the RMS value of the signal can be calculated, or peak-to-peak value.

The invention is not limited to the embodiment described herein which may be modified or varied without departing from the scope of the invention.

The invention claimed is:

1. An external defibrillator comprising:
   electrodes;
   a processor; and
   a circuit connecting the processor and the electrodes, wherein when the electrodes are in contact with a patient, the processor performs operations comprising:
   receiving electrical signals from the patient;
   determining, from the electrical signals, a signal (Z), wherein Z is a measure of transthoracic impedance of the patient;
   establishing an electrocardiogram (ECG) of the patient based on the electrical signals;
   determining, based on Z, when an interference condition is present and
   when the interference condition is present, inhibiting a shock delivery circuit from delivering a shock to the patient via the electrodes, based on Z, and independent of the ECG, for a defined period of time.

2. The external defibrillator of claim 1, wherein the determining when the interference condition is present further comprises forming a first derivative of Z with respect to a period of time ($Z^{(1st\ derivative)}$), deriving a quantity of interference related to $Z^{(1st\ derivative)}$, and determining if the quantity of interference exceeds a threshold level.

3. The external defibrillator of claim 2, wherein the quantity of interference is a measure of the number of times the amplitude of $Z^{(1st\ derivative)}$ exceeds the threshold level.

4. The external defibrillator of claim 2, wherein when the electrodes are in contact with the patient, the processor performs additional operations comprising:
   converting the signal Z from analog to digital, to yield a digital signal ($Z^{(A\ to\ D\ converted)}$); and
   using ($Z^{(A\ to\ D\ converted)}$) for the determining of when the interference condition is present.

5. The external defibrillator of claim 1, wherein the electrodes comprise a single pair of electrodes, and wherein the electrical signals are detected via the electrodes.

6. A method comprising:
   determining, via a processor, a transthoracic impedance from electrical data;
   calculating a first derivative of the transthoracic impedance for a time window;
   determining an average amplitude of the first derivative within the time window; and
   when the average amplitude is above a threshold:
   flagging the electrical data as having an interference; and
   preventing a diagnostic algorithm from detecting a shockable rhythm from the electrical data for a period of time.

7. The method of claim 6, further comprising iteratively repeating the determining of the transthoracic impedance, the calculating of the first derivative, and the determining of the average amplitude until the interference is no longer present.

8. The method of claim 6, wherein the period of time is four seconds.

9. The method of claim 6, wherein the period of time is 0.75 seconds.

10. The method of claim 6, wherein the electrical data is sampled at 170.66 samples per second.

11. The method of claim 6, further comprising identifying the shockable rhythm from the electrical data.

12. The method of claim 6, further comprising using a combination of a high pass filter and a low pass filter to determine the transthoracic impedance.

13. The method of claim 12, wherein the low pass filter removes a 30 kHz signal from the electrical data.

14. A defibrillator comprising:
   a shock circuit;
   a processor;
   electrodes; and a circuit connecting the processor and the electrodes, wherein when the electrodes are in contact with a patient, the processor performs operations comprising:
  receiving electrical signals;
  determining, from the electrical signals and using a high pass filter in combination with a low pass filter, a transthoracic impedance of the patient;
  establishing an electrocardiogram (ECG) of the patient based on the electrical signals;
  determining, based on the transthoracic impedance, when an interference condition is present; and
  when the interference condition is present, inhibiting the shock delivery circuit from delivering a shock via the electrodes, based on the ECG, for a defined period of time.

15. The defibrillator of claim 14, wherein a first derivative of the transthoracic impedance is taken with respect to a moving time window.

16. The defibrillator of claim 15, wherein the moving time window is based on a binary array size and a sample rate.

17. The defibrillator of claim 14, wherein when the electrodes are in contact with the patient, the processor performs additional operations comprising:
  when the interference condition is not present, allowing the shock delivery circuit to deliver the shock via the electrodes, based on the ECG.

18. The defibrillator of claim 14, wherein the high pass filter removes a direct current offset.

19. The defibrillator of claim 14, wherein the defined period of time is four seconds.

20. The defibrillator of claim 14, wherein the interference condition is determined to be present when an average amplitude of the first derivative in a time window is above a threshold in more than fifty percent of the time window.

\* \* \* \* \*